US009801582B2

(12) United States Patent
Ahmed

(10) Patent No.: US 9,801,582 B2
(45) Date of Patent: Oct. 31, 2017

(54) THIGH ADHESION QUANTITATIVE MEASUREMENT SYSTEM

(71) Applicant: KING SAUD UNIVERSITY, Riyadh (SA)

(72) Inventor: Mostafa Abdelhamid Mohamed Ahmed, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 235 days.

(21) Appl. No.: 14/940,093

(22) Filed: Nov. 12, 2015

(65) Prior Publication Data
US 2017/0135634 A1   May 18, 2017

(51) Int. Cl.
*A61B 5/00*   (2006.01)

(52) U.S. Cl.
CPC .......... *A61B 5/4869* (2013.01); *A61B 5/0004* (2013.01); *A61B 5/72* (2013.01); *A61B 5/742* (2013.01); *A61B 2562/0247* (2013.01)

(58) Field of Classification Search
CPC ................ A61B 5/6802; A61B 5/6831; A61B 2562/0247; A61B 2562/046; A61B 5/1036; A61B 5/442
See application file for complete search history.

(56) References Cited

U.S. PATENT DOCUMENTS

| 5,033,291 A | 7/1991 | Podoloff et al. |
| 5,225,959 A | 7/1993 | Stearns |
| 5,984,874 A * | 11/1999 | Cerwin ................... G01K 1/045 374/E1.008 |
| 6,474,367 B1 * | 11/2002 | Jayaraman ......... A41D 13/1236 139/383 R |
| 8,994,528 B2 | 3/2015 | Celik-Butler et al. |
| 2002/0171559 A1 * | 11/2002 | Yang ...................... H04B 1/202 340/12.3 |
| 2003/0212335 A1 | 11/2003 | Huang |
| 2005/0242767 A1 * | 11/2005 | Ho ........................... H02P 21/22 318/808 |
| 2007/0021682 A1 * | 1/2007 | Gharib ................. A61B 5/0488 600/546 |
| 2011/0208071 A1 | 8/2011 | Lu et al. |

(Continued)

FOREIGN PATENT DOCUMENTS

DE   10 2010 049 154 A1   6/2011

*Primary Examiner* — Sean Dougherty
(74) *Attorney, Agent, or Firm* — Richard C. Litman

(57) ABSTRACT

The thigh adhesion quantitative measurement system is a sensor system for precisely locating fibers and/or bands of connective tissue formed between layers of body tissue, binding the layers together and not permitting them to glide over each other. This bonding is called an adhesion. The present system is designed to determine quantitatively the degree of adhesion and the location of high-pressure adhesion(s) such that medical removal procedures (e.g., liposuction) can be precisely performed. The system makes use of a scanning device having an array of pressure sensors, the scanning device being defined by a flexible plate wrapped by a belt to a patient's limb, such as a thigh. A flexible cable connects the plate to a body-worn transmitter that wirelessly transmits real-time pressure distribution images received from the flexible plate to a computer for use by doctors preparing for the liposuction procedure.

7 Claims, 8 Drawing Sheets

(56) References Cited

U.S. PATENT DOCUMENTS

| | | | |
|---|---|---|---|
| 2012/0232578 A1 | 9/2012 | Altobelli et al. | |
| 2012/0283599 A1* | 11/2012 | Borja | A61F 2/4657 |
| | | | 600/587 |
| 2014/0039351 A1* | 2/2014 | Mix | A61B 5/1114 |
| | | | 600/587 |
| 2015/0363585 A1* | 12/2015 | Gooding | G06F 21/32 |
| | | | 726/19 |
| 2016/0296162 A1* | 10/2016 | Boken | A61B 5/6846 |

* cited by examiner

THIGH ADHESION QUANTITATIVE MEASUREMENT SYSTEM

BACKGROUND OF THE INVENTION

1. Field of the Invention

The present invention relates generally to biomedical sensors, and particularly to a thigh adhesion quantitative measurement system.

2. Description of the Related Art

Body structures have layers of connective tissue on their outer surfaces. These layers allow the different parts to glide over each other. Sometimes fibers and/or bands of connective tissue form between surfaces that should be separate. When connective tissue layers become bound together, that's called an adhesion. One type of adhesion is thigh adhesions, which cause inflammation of the adhesion area. This causes pain and other difficulties, especially during walking. The treatment of adhesions of the thighs usually requires a surgical procedure, for example, liposuction.

Thus, a thigh adhesion quantitative measurement system solving the aforementioned problems is desired.

SUMMARY OF THE INVENTION

The thigh adhesion quantitative measurement system is a sensor system for precisely locating fibers and/or bands of connective tissue formed between layers of body tissue that bind them together, not permitting them to glide over each other. This bonding is called an adhesion. The present system is designed to determine quantitatively the degree of adhesion and the location of high-pressure adhesion(s) such that medical removal procedures (e.g., liposuction) can be precisely performed. The system makes use of a scanning system having an array of pressure sensors, the scanning system being defined by a flexible plate wrapped by a belt to a patient's limb, such as a thigh. A flexible cable connects the plate to a body-worn transmitter that wirelessly transmits real-time pressure distribution images received from the flexible plate to a computer or other imaging device for use by doctors preparing for the liposuction procedure.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The thigh adhesion quantitative measurement system is a sensor system for precisely locating fibers and/or bands of connective tissue foil led between layers of body tissue, binding the layers together and not permitting them to glide over each other. This bonding is called an adhesion. The present system is designed to determine quantitatively the degree of adhesion and the location of high-pressure adhesion(s) such that medical removal procedures (e.g., liposuction) can be precisely performed. The system makes use of a scanning device (SD) having an array of pressure sensors, the scanning device (SD) being defined by a flexible plate wrapped by a belt to a patient's limb, such as a thigh. A flexible cable connects the plate to a body-worn transmitter that wirelessly transmits real-time pressure distribution images received from the flexible plate to a computer or other imaging device for use by doctors preparing for the liposuction procedure.

Figure 1:
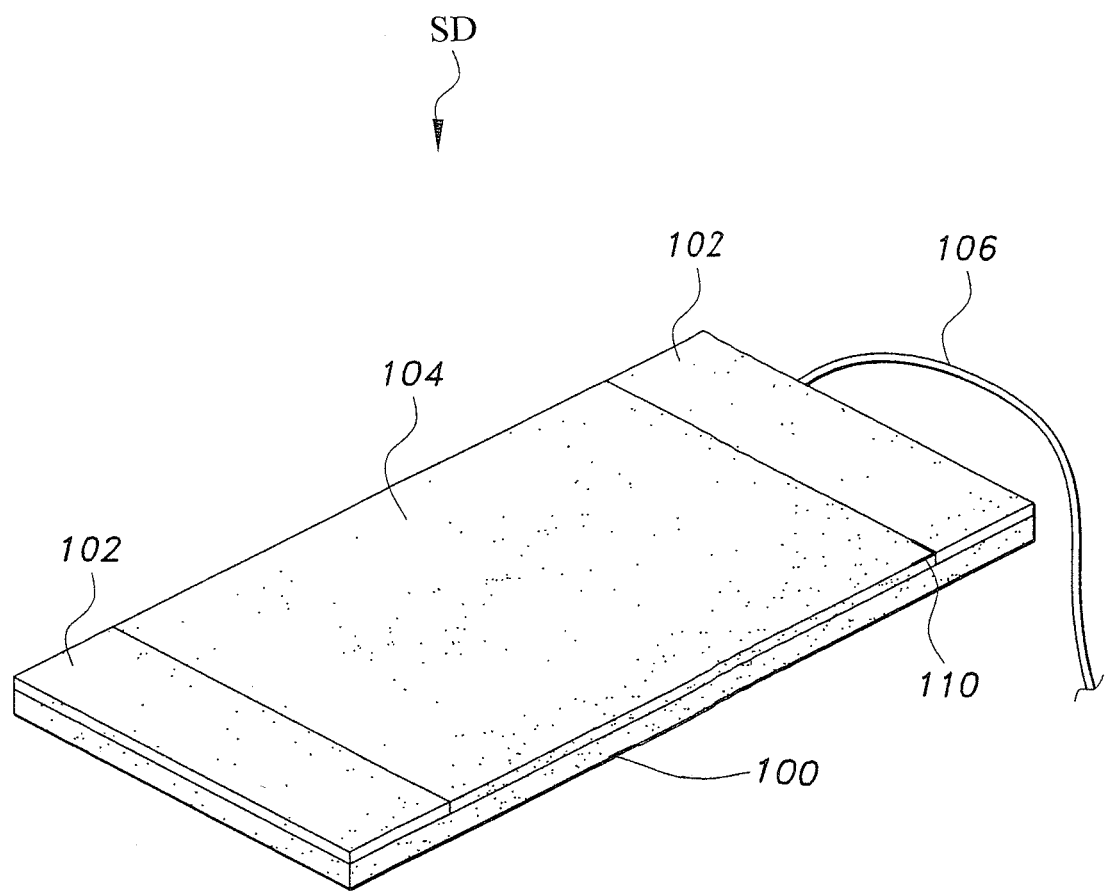
FIG. 1 is a perspective view of a flexible plate pressure sensor array for a thigh adhesion quantitative measurement system according to the present invention.
Figure 2:
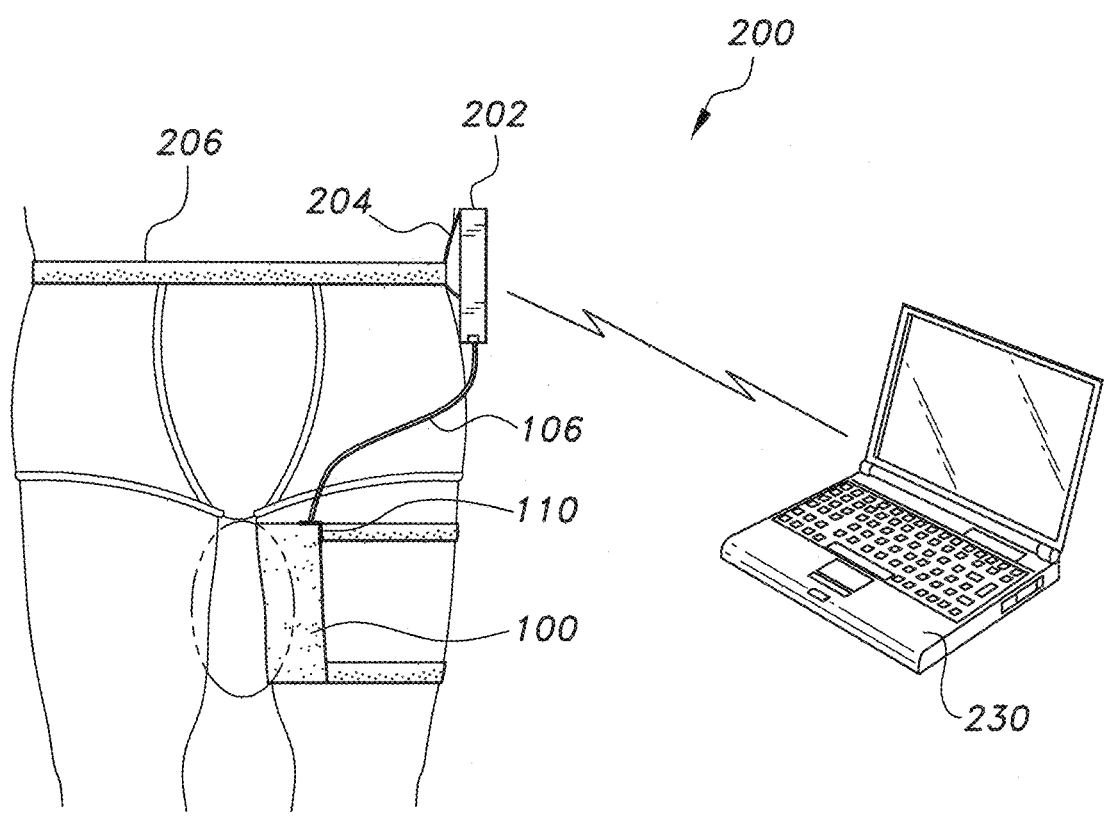
FIG. 2 is an environmental front view of a thigh adhesion quantitative measurement system according to the present invention, showing an exemplary mounting position of the pressure sensor array on a subject's thigh.

As shown in FIGS. 1 and 2, the system 200 includes a scanning device (SD) consisting of a flexible plate (planar) 100, an active sensor area 104 and two inactive areas 102 disposed on opposing ends of the flexible plate 100, which is wrapped by a sensor belt to one of the inner thighs of the patient, as shown in FIG. 2. It should be understood that any other adhesion region may be scanned using the scanning device (SD). The plate of the pressure sensor array 100 is connected via a cable 106 to a portable transmitter unit 202, which is mounted on the waist of the patient using a transmitter unit belt 206 and loop 204, the portable transmitter unit 202 wirelessly communicating with a remote laptop computer 230.

Figure 4:
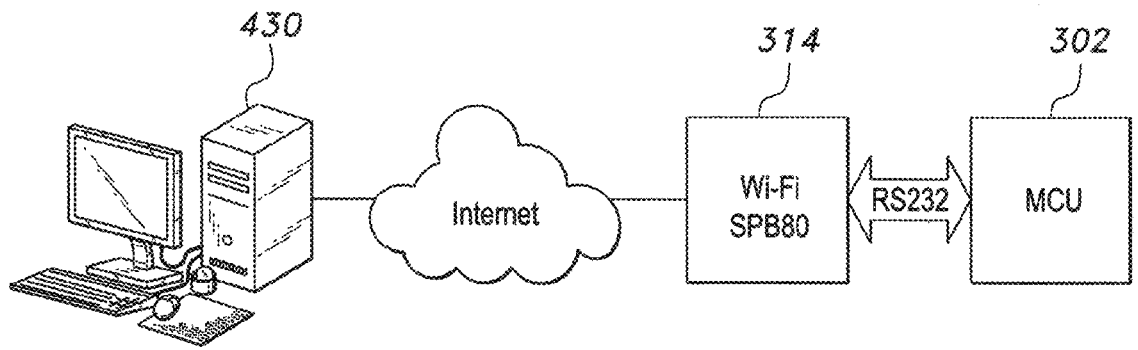
FIG. 4 is a block diagram of a wireless network connected to the controller of a thigh adhesion quantitative measurement system according to the present invention.

Two tests for each patient may be done. The first one is a static test, in which the patient stands with his legs near to each other until there is enough pressure between the thighs to do the liposuction. The other test is a dynamic test, in which the patient is asked to walk to get a view of the pressure profiles applied to the adhesion region during movement. In both tests, the two inner thighs will be in contact with each other in different degrees. This will apply different pressure profiles on the pressure sensor array plate. The pressure sensor array 104 will create real-time pressure distribution images of the scanned adhesion area. These images will be sent to the transmitter unit 202 via flexible cable 106. The transmitter unit 202 will process the acquired images and then send them wirelessly to a remote computer or other imaging device, such as desktop 430 (shown in FIG. 4) or laptop computer 230 (shown in FIG. 2). The remote computer (e.g., desktop 430 or laptop 230) will display color mapping pressure distribution images of the scanned adhesion area while the test is running. Thus, doctors can determine quantitatively the degree of adhesion and at which location in the scanned area the adhesion has occurred. This will help in predicting inflammation problems before it happens, determining the medical procedure required, and precisely determining the high pressure adhesion location for the surgeon to do the liposuction.

The pressure sensor array flexible plate 100 includes an active sensor area 104 and two inactive areas 102 disposed on opposing ends of the flexible plate pressure sensor array 100. A (0, 0) datum point 110 is defined on a lower right-hand corner of the active portion 104 of the flexible plate pressure sensor array 100. The spatial resolution and the active area of pressure sensors will determine the number of sensors used to scan the adhesion area. One possible design (exemplary without limitation) of the pressure sensor pressure sensor array 100, which will be referred to in the rest of the description for purposes of illustration, is as follows. The size of the active area of the pressure sensor array may be=256×128 mm. The active area of the pressure sensor array therefore equals 32,768 $mm^2$. The spatial resolution of the pressure sensor may be=4×8 mm. The area covered by single pressure sensor therefore equals 32 $mm^2$. The number of sensor elements=32,768÷32=1024 elements. The flexible plate pressure sensor array 100 will cover the adhesion area of interest to scan (e.g., the inner area of one of the thighs, as shown in FIG. 2). The datum point 110 in the flexible plate pressure sensor array 100 is used to correlate the spatial x, y zero point of the generated color-mapped pressure image with the actual sensor position over the scanned inner thigh of the subject. It should be understood that the present system contemplates different sizes of pressure sensor plates to cover different adhesion area sizes.

In the thigh adhesion quantitative measurement system, the active sensor area 104 covers the scanned adhesion area (the thigh, as shown in FIG. 2). The flexible plate pressure sensor array 100 is clearly shown attached to a front portion of the subject's thigh, and it continues to wrap around, covering a rear portion of the subject's thigh. The flexible plate pressure sensor array 100 is attached to the adhesion area using two belts disposed along opposite edges of the flexible plate 100. The flexible plate pressure sensor array 100 is connected to the transmitter unit 202 via a flexible connection cable 106. The transmitter unit 202 is attached on the patient waist using belt 206. The transmitter unit 202 will send the adhesion region pressure distribution images generated from the flexible plate pressure sensor array 100 wirelessly to a computer 430 for analyzing.

Before starting a new scanning session, the patient is asked to spread his legs such that minimum pressure is applied to the adhesion area. Then the system will record the pressure profile applied to the flexible plate pressure sensor array 100 as the zero pressure frame for this session. All read frames during scanning have to be subtracted from the zero pressure frame. This procedure readies the system for the two different patient tests described below.

The first test is a static test in which the patient is asked to stand with his legs near to each other until sufficient pressure registers over the adhesion region to do the liposuction. Next, the system will record the pressure applied to the pressure sensor array as the static pressure profile frame for this session. The recorded image will help the surgeon to precisely locate the high pressure adhesion area on the patient's scanned site, at which the liposuction process will be performed. After liposuction, the patient may be asked to repeat this test until a desired pressure profile in the scanned area is obtained indicating no further need for additional liposuction.

The second test is a dynamic test in which the patient is asked to walk. During walking, the adhesion area will apply time-moving pressure profiles over the flexible plate pressure sensor array 100. The system will display and record in real time the pressure profiles applied to the flexible plate pressure sensor array 100 as the dynamic pressure profiles for this session. This test yields a view of the problems encountered during walking in the adhesion region, and also aids prediction of inflammation problems before they occur. Moreover, performing the second test helps to determine the medical procedure required.

In the above tests, the generated pressure distribution images from the flexible plate pressure sensor array 100 are sent to the transmitter unit 202. The transmitter unit 202 has a Programmable System-on-Chip (PsoC) Microcontroller 302 (shown in FIG. 3) for processing (amplifying, filtering, offsetting, etc.) and digitizing the generated pressure distribution images, which are sent wirelessly as processed images to the computer for analysis by the specialist and saving to the patient database.

Figure 3:
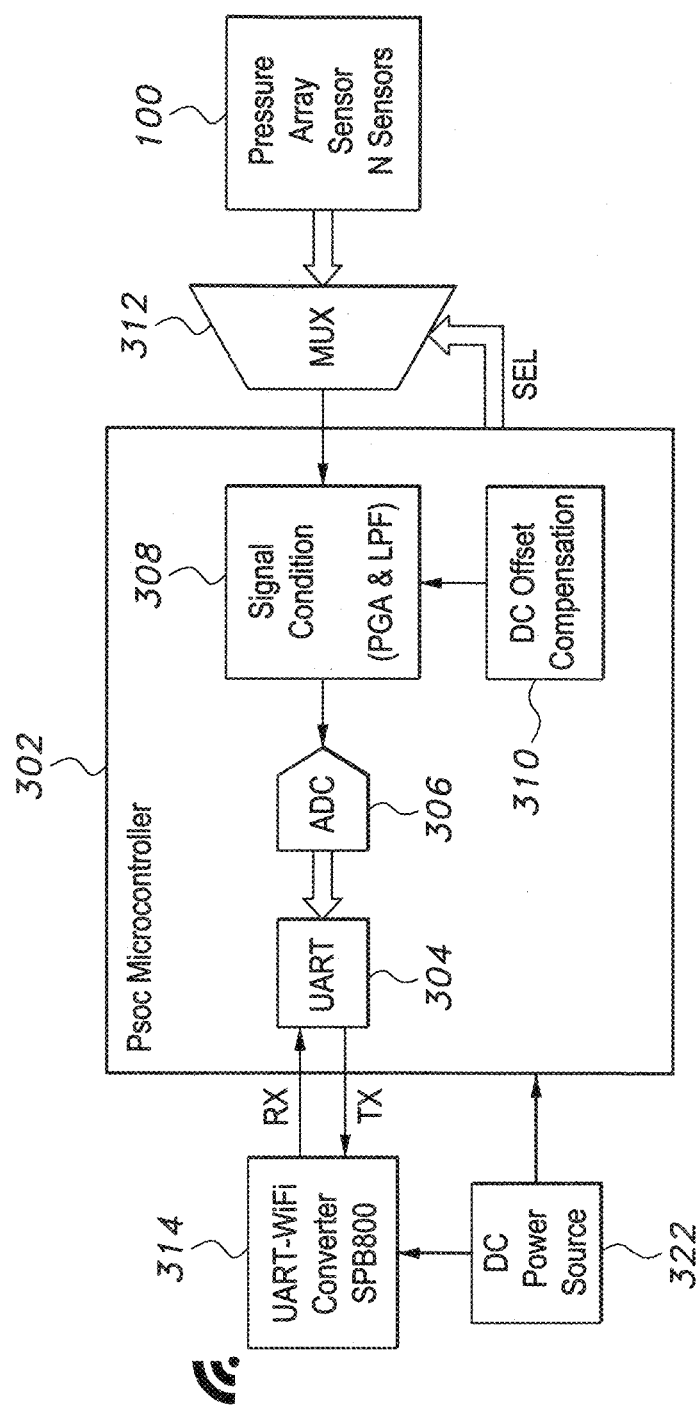
FIG. 3 is a block diagram of a transmitter unit of a thigh adhesion quantitative measurement system according to the present invention.

In general, the scanning means utilizes a processor, such as a PSoC microcontroller 302, shown in FIG. 3. The PSoC microcontroller 302 includes a Universal Asynchronous Receiver-Transmitter (UART) 304 connected to an analog-to-digital converter 306, which is connected to a signal conditioner 308. A DC offset compensator 310 is connected to the signal conditioner 308. The flexible plate pressure sensor array 100 is connected to a multiplexer 312, which, in turn, feeds the signal conditioner 308 of the PSoC microcontroller 302. The N×1 multiplexer 312 is controlled by select SEL signals from the PSoC microcontroller 302. The pressure array sensor 100 has N sensors in the array. The N analog signal outputs from the flexible plate pressure sensor array 100 are input into the analog multiplexer 312 (MUX). The output of the analog MUX 312 is input into the PSoC microcontroller 302. The microcontroller 302 sends the MUX select inputs to scan the N elements of the flexible plate pressure sensor array 100 continuously. The microcontroller 302 comprises a signal conditioner 308, a DC offset compensator 310, an 8-bit-ADC 306, and a UART 304 for connection to a UART-WiFi converter 314. The sensor signal output from the MUX 312 is input to the microcontroller signal conditioner 308 that conditions (e.g., by amplification with a programmable gain amplifier (PGA) and/or filtering with a low pass filter (LPF)) the input, which may also require a DC offset applied by the DC offset compensator 310. Thereafter, the signal enters the ADC 306 for digitization to get pressure readings (N bytes) from the subject's thigh. Data from the ADC 306 is sent to the UART 304. The ADC data is sent outside the microcontroller via the UART interface part of PsoC microcontroller 302 at a suitable baud rate. flexible plate pressure sensor array 100 of FIG. 3 interfaces to the pressure scanning display computer 430 (shown in FIG. 4) using a wireless connection, e.g., WiFi transceiver 314, such that the pressure profile of the subject's thigh can be transferred to the pressure scanning display computer 430 over an intranet or other network in a preferably wireless manner. The PSoC UART 304 interfaces to the external UART to WiFi converter 314 (e.g., SPB800) such that the pressure profile images can be transferred wirelessly to the computer. The SPB800 module has a high performance chip antenna as the primary RF interface. The module sends digitized adhesion area pressure distribution images read from MCU 302 to an external computer and receives commands from the external computer while forwarding the commands to MCU 302.

The following specification and parameters are merely illustrative. For example, the MUX 312 may have a high impedance input, input signals rail-to-rail, and a number of inputs up to N. The signal conditioner 308 may be a PGA having a high impedance input, wide bandwidth, low offset output voltage, and up to thirty-three user-programmable gain settings with a maximum gain of 48.0.

Alternatively, the signal conditioner 308 may be an LPF (low pass filter) having a programmable corner frequency and damping ratio with no external components, and it may be second order.

The ADC 306 may have an 8-bit resolution with single-ended/differential input, using an unsigned data format with a sample rate up to 500K samples per second, and an input range defined by an internal reference of the PSoC microcontroller 302. The power source 322 is connected to the WiFI converter 314 and the PsoC microcontroller 302, and may be a battery providing 3.6 volt at approximately 1,800 mA, or the like. The UART 304 is a standard serial communication, asynchronous receiver and transmitter having burst rates up to 6 Mbits/second. Data framing consists of start, optional parity, and stop bits.

Figure 5A:
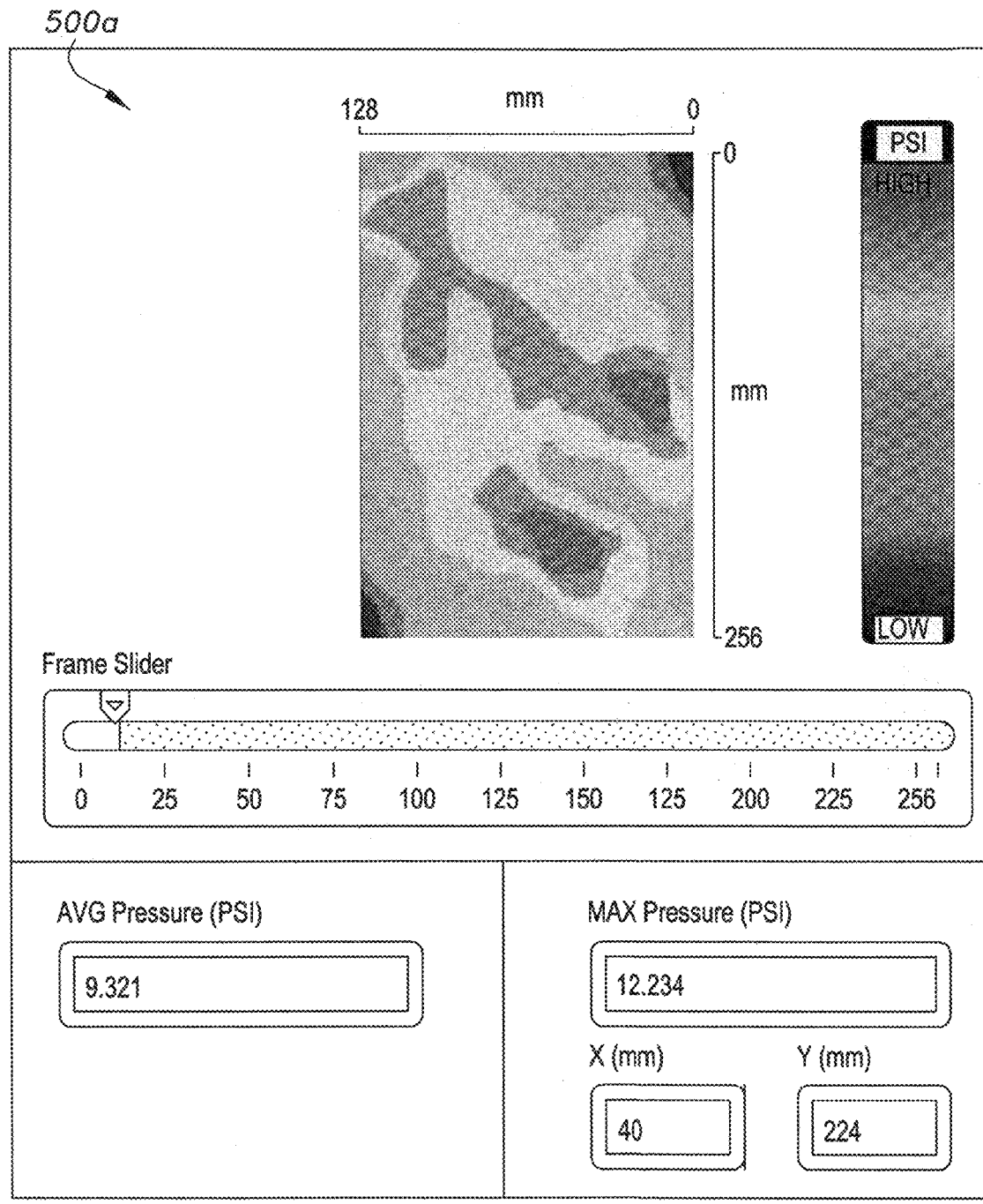
FIG. 5A is an exemplary screenshot showing images and data produced by a thigh adhesion quantitative measurement system according to the present invention.
Figure 5B:
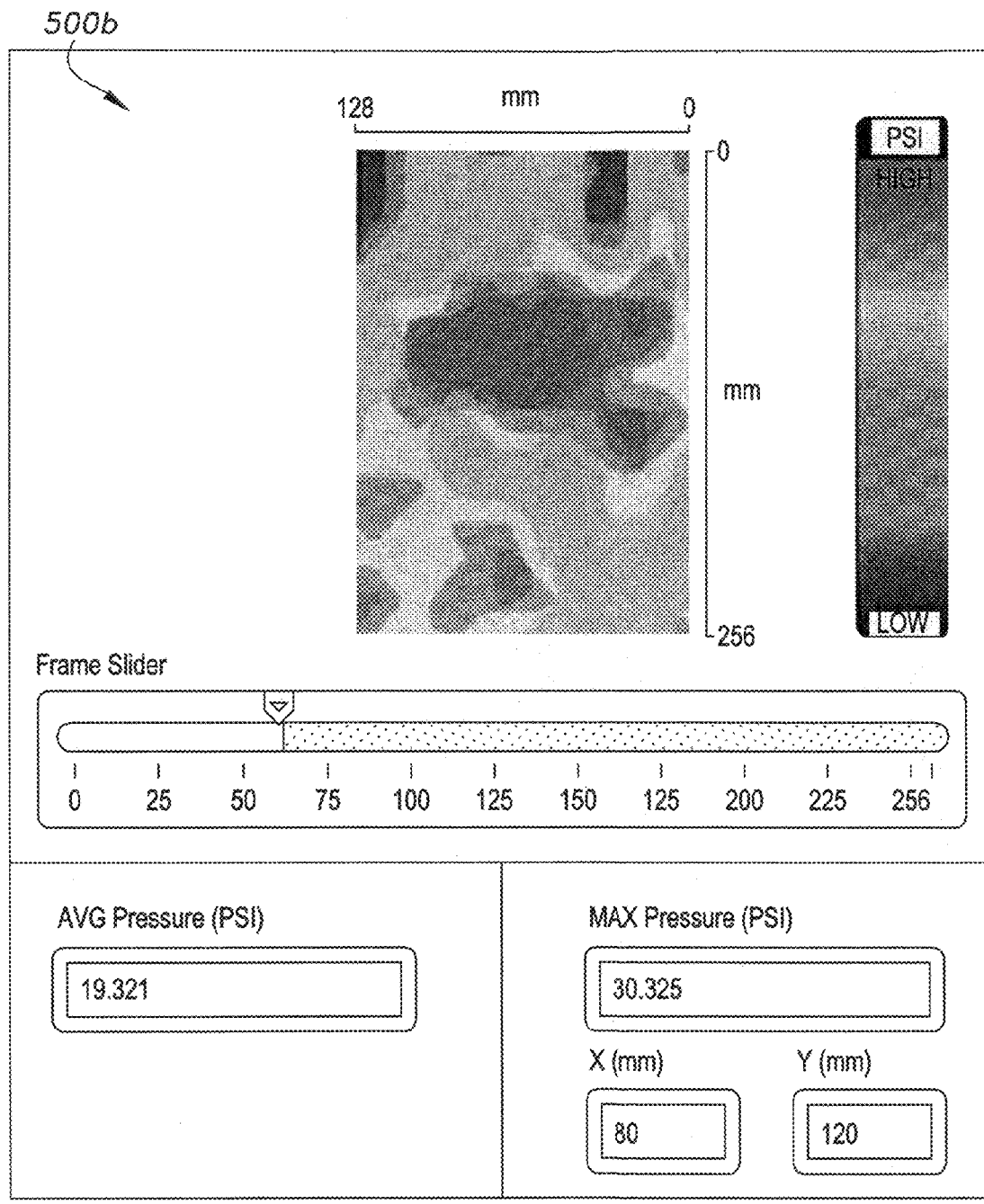
FIG. 5B is another exemplary screenshot showing images and data produced by a thigh adhesion quantitative measurement system according to the present invention.

With a pressure sensor array size=128 mm×256 mm, the pressure distribution images read from the transmitter unit 314 are displayed in an application program as color-mapped pressure distribution images (500a and 500b of FIGS. 5A and 5B). The pressure value at each point in the scanned adhesion area can be determined from the pressure color-coded values. From these images, the problems encountered in the adhesion region can be quantitatively analyzed to determine the proper treatment method.

Figure 6:
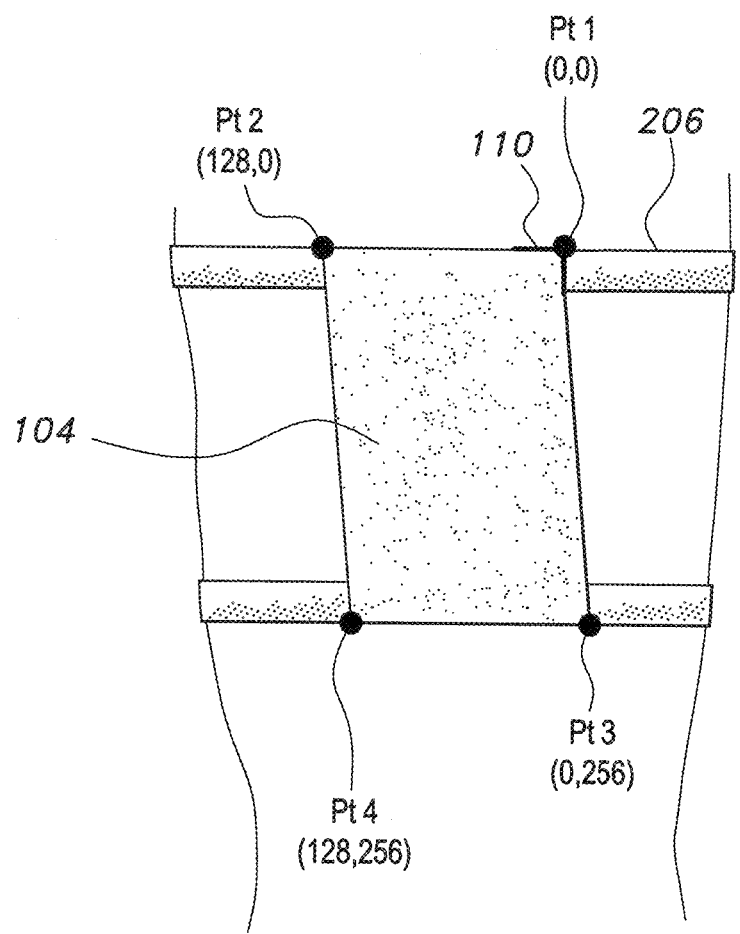
FIG. 6 is an environmental side view of the flexible plate pressure sensor array of FIG. 1, positioned to scan the inner thigh.

From image maps 500a and 500b of FIGS. 5A and 5B, the high pressure value in the adhesion area is at point (x,y)= (80,120) mm. We can easily find this point on the patient's scanned thigh. To locate this point, and before removing the flexible plate pressure sensor array 100 from the scanned thigh, a body marker is used to make a clear mark on four points (Pt1 at sensor array datum coordinates (0,0), Pt2 at sensor array coordinates (128,0), Pt3 at sensor array coordinates (0,256), Pt4 at sensor array coordinates (128,256) at the four corner edges of the used pressure sensor array active portion 104, as shown in FIG. 6.

Figure 7:
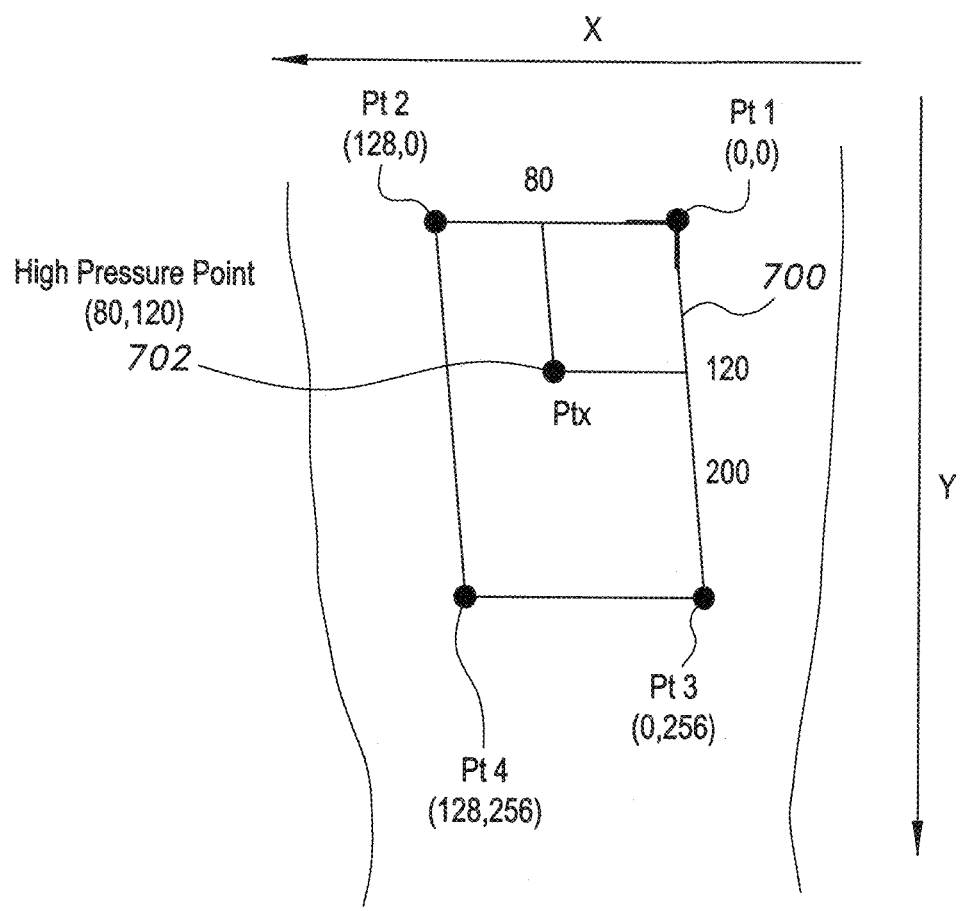
FIG. 7 is a diagram showing the location of a high pressure adhesion area to be scanned by the system of FIG. 6.

Next, remove the flexible plate pressure sensor array 100 from the scanned thigh, and using the body marker, draw lines on the subject's body between (Pt1 and Pt2), (Pt2 and Pt4), (Pt3 and Pt4) and (Pt1, Pt3). The drawn lines define an outline 700 of where the active sensor region 104 was placed on the subject's body. Using a ruler, find a point in the line between (Pt1 and Pt3), this point being below Pt1 by 120 mm. Using a ruler find a point in between (Pt1 and Pt3), this point being below Pt1 by 120 mm. Using a ruler find a point in the line between (Pt1 and Pt2), this point being apart from Pt1 by 80 mm, as shown in FIG. 7. Thus, the high pressure point (80,120) 702 is defined on the subject's body. By this technique, it is readily determined precisely the place or the region that needs to be liposuctioned by a surgeon.

It is to be understood that the present invention is not limited to the embodiments described above, but encompasses any and all embodiments within the scope of the following claims.

I claim:

1. A thigh adhesion quantitative measurement system, comprising:
   a processor;
   a scanning device, the scanning device consisting of a flexible plate and a flexible plate pressure sensor array disposed thereon and in operable communication with the processor, the flexible plate pressure sensor array having a central active sensor area and two inactive areas disposed on opposing ends of the central active sensor area, a (0,0) datum coordinate marker disposed on a corner of an active portion of the central active sensor area, the scanning device conforming to and taking pressure readings of the inner thigh region of a subject's body, sensor belts extending from opposite edges of the scanning device to secure the scanning device to the subject's inner thigh region;
   means for digitizing the pressure readings taken by the scanning device to obtain a pressure profile providing indicia of high pressure points within the region;
   a wireless data converter in operable communication with the processor; and
   a pressure scanning display computer in communication with the wireless data converter, the pressure scanning display computer having a screen for displaying the pressure profile as images, wherein the pressure profile images are presented as a color map of pressure over the subject's inner thigh region.

2. The thigh adhesion quantitative measurement system according to claim 1, further comprising a multiplexer connected between the scanning device and the processor, the multiplexer selecting inputs to scan elements of the pressure sensor continuously into the processor.

3. The thigh adhesion quantitative measurement system according to claim 2, wherein the processor further comprises a signal conditioner circuit for conditioning the pressure data before the data is digitized.

4. The thigh adhesion quantitative measurement system according to claim 3, wherein the signal conditioner circuit is selected from the group consisting of a programmable gain amplifier circuit and a low pass filter circuit.

5. The thigh adhesion quantitative measurement system according to claim 3, further comprising a DC offset compensator connected to the signal conditioner circuit.

6. The thigh adhesion quantitative measurement system according to claim 1, further comprising a connection cable extending from the flexible plate and attachable to the processor, the connection cable facilitating operable communication of the scanning device with the processor.

7. The thigh adhesion quantitative measurement system according to claim 1, further comprising:
   a transmitter unit belt; and
   a transmitter unit belt loop disposed on a housing of the wireless data converter, the transmitter unit belt being threaded through the transmitter unit belt loop to secure the wireless data converter to the subject's body.

* * * * *